(12) United States Patent
Fuerst et al.

(10) Patent No.: US 11,369,440 B2
(45) Date of Patent: Jun. 28, 2022

(54) TACTILE AUGMENTED REALITY FOR MEDICAL INTERVENTIONS

(71) Applicant: THE JOHNS HOPKINS UNIVERSITY, Baltimore, MD (US)

(72) Inventors: Bernhard Fuerst, Baltimore, MD (US); Greg M. Osgood, Baltimore, MD (US); Nassir Navab, Baltimore, MD (US); Alexander Winkler, Baltimore, MD (US)

(73) Assignee: THE JOHN HOPKINS UNIVERSITY, Baltimore, MD (US)

(*) Notice: Subject to any disclaimer, the term of this patent is extended or adjusted under 35 U.S.C. 154(b) by 377 days.

(21) Appl. No.: 16/605,421

(22) PCT Filed: Mar. 30, 2018

(86) PCT No.: PCT/US2018/025569
§ 371 (c)(1),
(2) Date: Oct. 15, 2019

(87) PCT Pub. No.: WO2018/194822
PCT Pub. Date: Oct. 25, 2018

(65) Prior Publication Data
US 2021/0121243 A1    Apr. 29, 2021

Related U.S. Application Data

(60) Provisional application No. 62/486,035, filed on Apr. 17, 2017.

(51) Int. Cl.
*A61B 34/00* (2016.01)
*A61B 34/10* (2016.01)
(Continued)

(52) U.S. Cl.
CPC .............. *A61B 34/25* (2016.02); *A61B 34/10* (2016.02); *G06F 3/011* (2013.01); *G06F 3/017* (2013.01);
(Continued)

(58) Field of Classification Search
CPC ....................................................... A61B 34/25
(Continued)

(56) References Cited

U.S. PATENT DOCUMENTS

| 6,608,628 B1 * | 8/2003 | Ross | G16H 40/67 |
| | | | 345/619 |
| 9,052,710 B1 * | 6/2015 | Farwell | B25J 9/1656 |

(Continued)

OTHER PUBLICATIONS

PCT International Search Report and Written Opinion dated Jun. 7, 2018 in corresponding International Application No. PCT/US2018/025569, pp. 1-13.
International Preliminary Report on Patentability in International Application No. PCT/US2018/025569 dated Oct. 22, 2019, 6 pages.

*Primary Examiner* — Javid A Amini
(74) *Attorney, Agent, or Firm* — MH2 Technology Law Group, LLP

(57) ABSTRACT

A system for modelling a portion of a patient includes a processing unit, a manipulator, a sensor, and a display device. The processing unit is configured to receive patient data and to process the patient data to generate a model of the portion of the patient. The sensor is configured to capture manipulator data. The processing unit is configured to receive the manipulator data from the sensor and to process the manipulator data to determine a position of the manipulator, an orientation of the manipulator, or both. The display device is configured to display the model on or in the manipulator.

22 Claims, 4 Drawing Sheets

(51) Int. Cl.
*G06T 19/00* (2011.01)
*G06T 19/20* (2011.01)
*G16H 50/50* (2018.01)
*G16H 10/60* (2018.01)
*G16H 30/40* (2018.01)
*G16H 40/63* (2018.01)
*G06F 3/01* (2006.01)
*G06F 3/03* (2006.01)

(52) U.S. Cl.
CPC .......... *G06F 3/0317* (2013.01); *G06T 19/006* (2013.01); *G06T 19/20* (2013.01); *G16H 10/60* (2018.01); *G16H 30/40* (2018.01); *G16H 40/63* (2018.01); *G16H 50/50* (2018.01); *A61B 2034/104* (2016.02); *A61B 2034/105* (2016.02); *A61B 2034/254* (2016.02); *G06T 2210/41* (2013.01); *G06T 2219/2016* (2013.01)

(58) Field of Classification Search
USPC ....................................................... 345/156
See application file for complete search history.

(56) References Cited

U.S. PATENT DOCUMENTS

| | | | |
|---|---|---|---|
| 2008/0088529 A1* | 4/2008 | Tang | G02B 27/0172 345/8 |
| 2011/0128555 A1* | 6/2011 | Rotschild | G06F 3/017 356/625 |
| 2013/0325181 A1* | 12/2013 | Moore | B25J 13/08 700/259 |
| 2014/0022283 A1* | 1/2014 | Chan | G06F 3/147 345/633 |
| 2015/0094855 A1* | 4/2015 | Chemouny | B25J 9/023 700/259 |
| 2015/0248793 A1* | 9/2015 | Abovitz | A63F 13/428 345/633 |
| 2016/0249989 A1* | 9/2016 | Devam | G09B 21/009 345/633 |
| 2016/0256101 A1* | 9/2016 | Aharoni | A61B 5/150503 |
| 2017/0069120 A1* | 3/2017 | Benner | G06T 11/60 |
| 2017/0084027 A1* | 3/2017 | Mintz | A61B 1/005 |
| 2018/0193102 A1* | 7/2018 | Inoue | A61B 1/018 |
| 2020/0242767 A1* | 7/2020 | Zhao | A61B 6/50 |

* cited by examiner

TACTILE AUGMENTED REALITY FOR MEDICAL INTERVENTIONS

CROSS-REFERENCE TO RELATED APPLICATIONS

This application is a national stage conversion under 35 U.S.C. § 371 of PCT Application No. PCT/US2018/025569 entitled "TACTILE AUGMENTED REALITY FOR MEDICAL INTERVENTIONS" filed Mar. 30, 2018, which claims priority to U.S. Provisional Patent Application No. 62/486,035, filed Apr. 17, 2017, the entireties of which are incorporated herein by reference.

FIELD OF THE INVENTION

The present invention relates generally to a tactile augmented reality for use during medical interventions. More particularly, the present invention relates to a three-dimensional (3D) model of at least a portion of a patient that may be viewed by a surgeon during surgery.

BACKGROUND OF THE INVENTION

In the past, a surgeon was limited to viewing two-dimensional (2D) images (e.g., X-rays) of a patient before or during surgery. More recently, 3D printing has enabled surgeons to construct 3D models of a portion of the patient to better help the surgeon understand the anatomy of the patient. However, it may be time-consuming and expensive to construct the 3D models. In addition, the models need to be sterilized prior to entering the operating room. What is needed is an improved system and method for modelling a portion of a patient before or during surgery.

SUMMARY OF THE INVENTION

A system for modelling a portion of a patient is disclosed. The system includes a processing unit, a manipulator, a sensor, and a display device. The processing unit is configured to receive patient data and to process the patient data to generate a model of the portion of the patient. The sensor is configured to capture manipulator data. The processing unit is configured to receive the manipulator data from the sensor and to process the manipulator data to determine a position of the manipulator, an orientation of the manipulator, or both. The display device is configured to display the model on or in the manipulator.

A method for modelling a portion of a patient is also disclosed. The method includes receiving patient data from a medical imaging device. The patient data is processed to generate a model of the portion of the patient. Manipulator data is received from a sensor. The manipulator data is processed to determine a position of a manipulator, an orientation of the manipulator, or both. The manipulator is displayed on a display device using the processed patient data and the processed manipulator data. The model appears on or in the manipulator when the manipulator is displayed on the display device.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Figure 1:
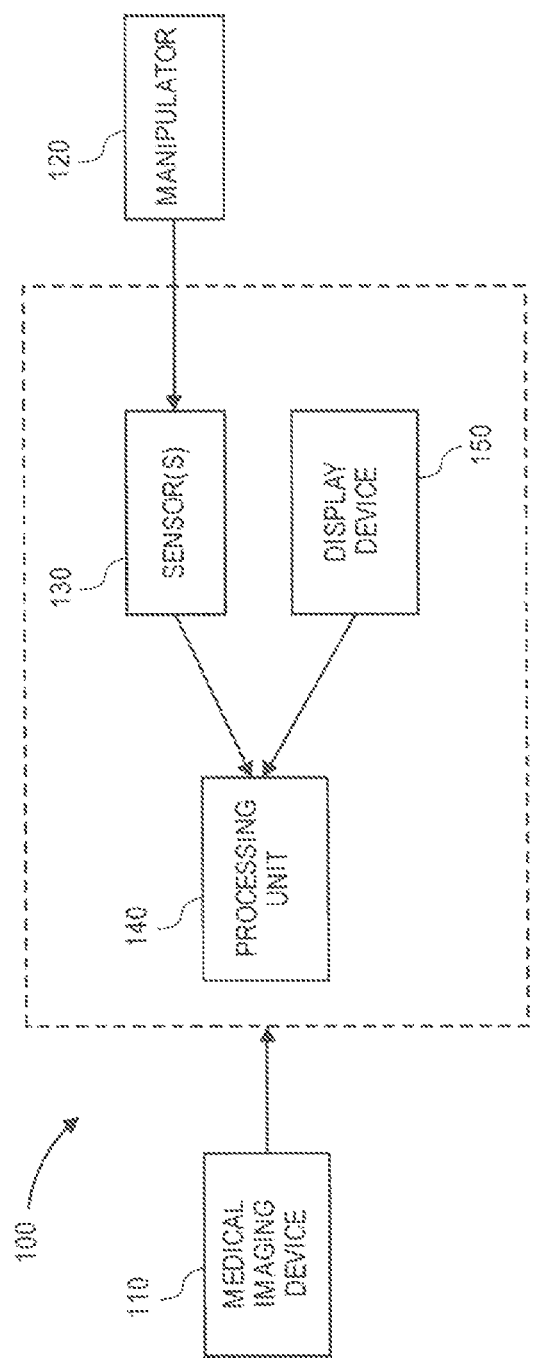
FIG. 1 illustrates a schematic view of a system for modelling at least a portion of a patient.

FIG. 1 illustrates a schematic view of a system 100 for modelling at least a portion of a patient. The system 100 may include a medical imaging device 110. The medical imaging device 110 may be or include an ultrasound device, a computed tomography (CT) scanner, a magnetic resonance imaging (MRI) scanner, a single-photon emission computed tomography (SPECT) scanner, a positron emission tomography (PET)/CT scanner, a PET/MR scanner, an optical coherence tomography (OCT) scanner, an X-ray scanner, a fluoroscope, or the like. The medical imaging device 110 may be configured to capture patient data.

The system 100 may also include a tactile manipulator 120. As described in greater detail below, a model of at least a portion of the patient may be displayed on/in the manipulator 120. The model may be a 2D model (e.g., an image) or a 3D model.

The system 100 may also include one or more sensors 130. The sensors 130 may be or include cameras, magnetic sensors, or other tracking devices configured to capture manipulator data.

The system 100 may also include a processing unit 140. The processing unit 140 may receive the patient data from the medical imaging device 110 and/or the manipulator data from the sensors 130. The processing unit 140 may process the patient data to generate one or more 2D or 3D models of at least a portion of the patient either before surgery or during surgery (e.g., in real-time). The processing unit 140 may also process the manipulator data to determine the position and orientation of the manipulator 120 (e.g., relative to the sensors 130).

The system 100 may also include a display device 150. The display device 150 may receive the processed patient data and/or the processed manipulator data from the processing unit 140. The combination of this data may enable a user to view a model of a portion of the patient on/in the manipulator 120 when the manipulator 120 is viewed through the display device 150. As described below, in one embodiment, the display device 150 may be or include a television, a computer monitor, a tablet, a smart phone, or the like. In another embodiment, the display device 150 may be configured to be mounted on the head of the user (e.g., a surgeon). For example, the display device 150 may be or include glasses, goggles, or the like that may at least partially cover one or both of the user's eyes. The display device 150 may include transparent lenses.

In at least one embodiment, the sensors 130, the processing unit 140, the display device 150, or a combination thereof may all be part of a single apparatus (e.g., that is configured to be mounted on the user's head). In at least one embodiment, the manipulator 120, the sensors 130, the processing unit 140, the display device 150, or a combination thereof may be sterilized and placed in the operation room together with the user and the patient.

Figure 2:
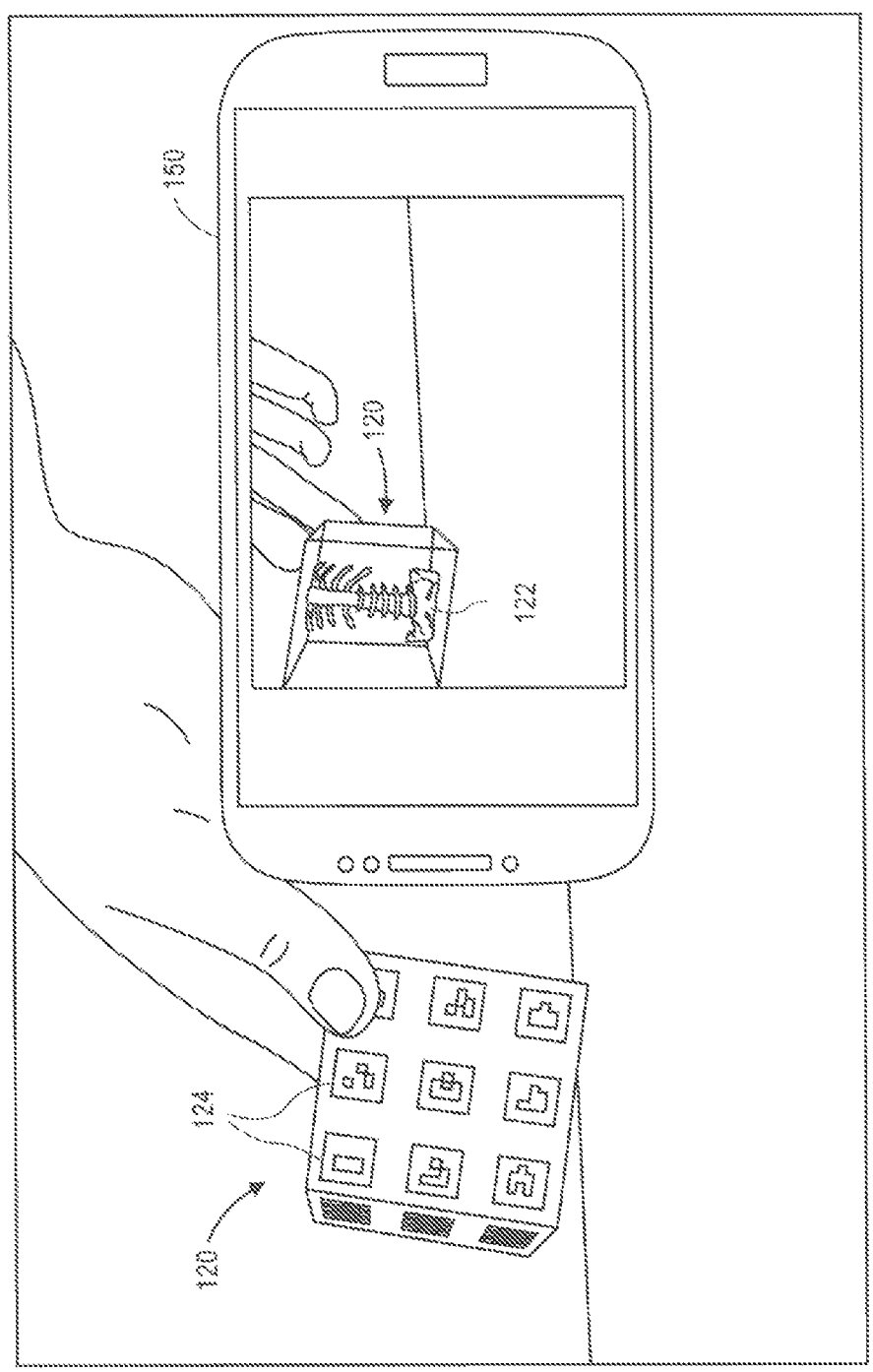
FIG. 2 illustrates a perspective view of a model appearing on/in the manipulator when the manipulator is viewed through a display device.

FIG. 2 illustrates a model 122 appearing on/in the manipulator 120 when the manipulator 120 is viewed through the display device 150. As shown, the manipulator 120 may be in the form of a cube. In other embodiments, the manipulator 120 may be in the form of a sphere or any other shape. The manipulator 120 may have visual markers 124 on an outer surface thereof. In the example shown, each side of the cube may have nine visual markers 124 (e.g., in a 3×3 configuration); however, as will be appreciated, the number, positioning, and type of visual markers may vary. The visual markers 124 may be or include digital markers, such as bar codes or the like.

When looking into/through the display device 150, the visual markers 124 on the outer surface of the manipulator 120 may not be visible. Instead, the visual markers 124 may enable the model 122 to appear on the outer surface the manipulator 120. More particularly, the virtual data (i.e., the model 122) aligns with the real world object (i.e., the manipulator 122). The visual markers 124 act as a surrogate that is replaced by a virtual object (i.e., the model 122) that is aligned with the tracked object (i.e., the manipulator 122) and accurately overlays or occludes the virtual markers 124 in the augmented view through the display device 150. In some embodiments, the model 122 may appear to be within the manipulator 120. In the example shown, the model 122 is a portion of a skeletal structure of the patient captured by the medical imaging device 110 and processed by the processing unit 140; however as will be appreciated, in other embodiments, the model 122 may include soft tissues, etc.

In at least one embodiment, the rendering of the patient data may be directly based on, for example, a volume rendering via raycasting, or indirectly through a segmentation preprocessing step to convert the volume data into surface meshes. If there is a calibration between the sensor 130 and the display device 150 (i.e., the relationship between the sensor 130 and the display device 150 is known), and the relationship between the visual markers 124 and the sensor 130 may be determined (e.g., estimated), the system 100 may accurately overlay virtual objects (e.g., the model 122) over the visual markers 124 on/via the display device 150.

Figure 3:
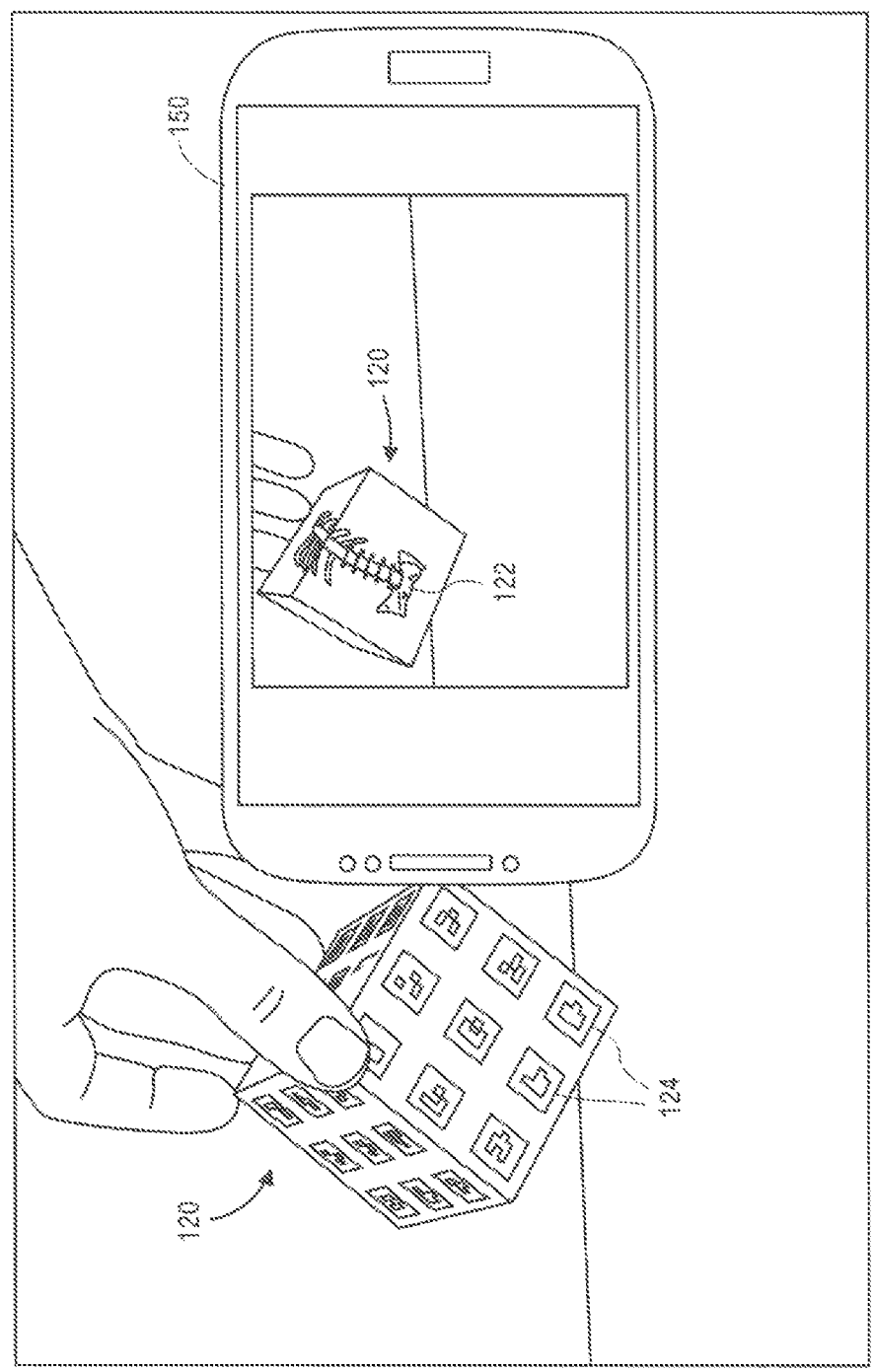
FIG. 3 illustrates a perspective view of the model rotating together with the manipulator when the manipulator is viewed through the display device.

FIG. 3 illustrates the model 122 rotating together with the manipulator 120 when the manipulator 120 is viewed through the display device 150. The model 122 may be fixed with respect to the manipulator 120. Thus, as described in greater detail below, the position and orientation of the model 122 changes together with the position and orientation of the manipulator 120. This may be seen by comparing FIGS. 2 and 3.

Figure 4:
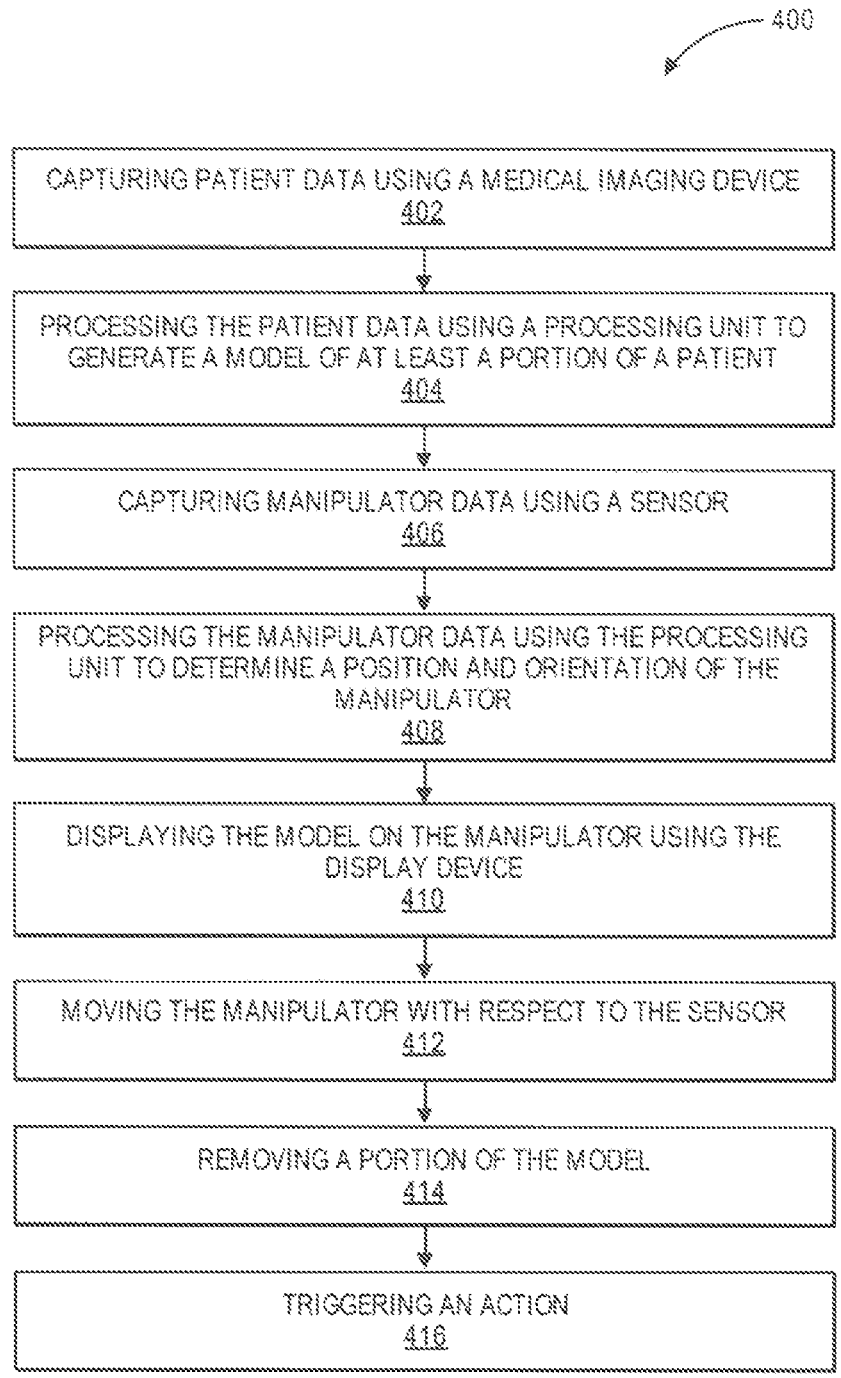
FIG. 4 illustrates a flowchart of a method for modelling at least a portion of a patient.

FIG. 4 illustrates a flowchart of a method 400 for modelling at least a portion of a patient. The method 400 may include capturing patient data using the medical imaging device 110, as at 402. The method 400 may also include processing the patient data using the processing unit 140 to generate a model 122 of at least a portion of the patient, as at 404.

The method 400 may also include capturing manipulator data using the sensor 130, as at 406. The method 400 may also include processing the manipulator data using the processing unit 140 to determine the position and orientation of the manipulator 120 (e.g., with respect to the sensor 130 and/or the display device 150), as at 408. The manipulator data may be captured and processed in real-time so that movement of the manipulator 120 by the user is synchronized with movement of the manipulator 120 (and the model 122) on the display device 150, as described below. The patient data and/or the manipulator data may be transmitted to the processing unit 140 through one or more wires or wirelessly.

The method 400 may also include displaying the model 122 using the manipulator 120, the display device 150, or a combination thereof, as at 410. More particularly, the manipulator 120 may be displayed on the display device 150 (e.g., using the processed manipulator data), and the model 122 may appear on and/or in the manipulator 120 (e.g., using the processed patient data and/or the processed manipulator data), as shown in FIGS. 2 and 3.

The method 400 may also include moving the manipulator 120 with respect to the sensor 130, as at 412. Moving the manipulator 120 may include changing the orientation of the manipulator 120 (e.g., by rotating the manipulator 120 about one, two, or three axes). As seen by comparing FIGS. 2 and 3, the model 122 is fixed with respect to the manipulator 120. As a result, the orientation of the model 122 changes together with the orientation of the manipulator 120. Moving the manipulator 120 may also or instead include changing the position of the manipulator 120. This may include moving the manipulator 120 side-to-side or up and down with respect to the sensor 130. As discussed above, the model 122 is fixed with respect to the manipulator 120. As a result, the model 122 may remain on/in the manipulator 120 as the manipulator 120 moves. Changing the position of the manipulator 120 may also include varying the distance between the manipulator 120 and the sensor 130. The manipulator 120 and the model 122 may appear larger in the display device 150 when the manipulator 120 is moved toward the sensor 130, and the manipulator 120 and the model 122 may appear smaller in the display device 150 when the manipulator 120 is moved away from the sensor 130.

The method 400 may also include removing (e.g., temporarily hiding) a portion of the model 122, as at 414. The user may select the portion of the model 122 to be removed by selecting (e.g., touching, tapping, etc.) it on the manipulator 120, the processing unit 140, or the display device 150. In at least one embodiment, removing a portion of the model 122 may include slicing the model 122 through a plane and removing the portion of the model 122 on one side of the plane. Alternatively, the user may select the portion of the model 122 to remain by selecting (e.g., touching, tapping, etc.) it on the manipulator 120, the processing unit 140, or the display device 150. The remaining portion of the model 122 may be increased in size.

The method 400 may also include triggering an action, as at 416. The action may be or include loading the model 122 on the manipulator 120, re-acquiring data, saving the view of the manipulator 120 and model 122 as a screenshot, saving other data, saving the current view as a video, requesting a remote consultation (e.g., a video call), or the like. The action may be triggered by making a gesture with the manipulator 120 (e.g., shaking the manipulator 120), touching/clicking a virtual button on the manipulator 120, or the like. Visualization of the model 122 may be updated in real-time following the user's input. The user's input may include changing the position and/or orientation of the manipulator 120, re-acquiring X-ray images, etc.

In one example, if the user removes a portion of the patient (e.g., a malignant tumor), the model 122 may have the corresponding portion removed. In another example, the user's hand or surgical instrument may appear in the model 122 as the user is performing surgery on the patient.

The steps above can be carried out using a non-transitory computer readable medium loaded onto a computing device such as a personal computer, tablet, phablet, smartphone, computer server, or any other computing device known to or conceivable by one of skill in the art. Indeed, any suitable hardware and software known to or conceivable by one of skill in the art could be used. The non-transitory computer readable medium can also be incorporated into the device for assessment of PAT.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for modelling a portion of a patient, comprising:
   a manipulator;
   a sensor configured to capture manipulator data, wherein the manipulator data comprises images or video of the manipulator;
   a processing unit configured to:
      receive the manipulator data from the sensor and to process the manipulator data to determine a position of the manipulator, an orientation of the manipulator, or both; and
      receive patient data comprising one or more images captured by a medical imaging device of first and second patients, and wherein the processing unit is also configured to process the patient data for the first and second patients and to generate a first model for the first patient and a second model for the second patient; and
   a display device configured to:
      display the first model on or in the manipulator when analyzing the first patient; and
      display the second model on or in the same manipulator when analyzing the second patient.

2. The system of claim 1, wherein the manipulator comprises one or more visual markers on an outer surface thereof that enable the first and second models to appear in the manipulator when the manipulator is displayed on the display device, and wherein the one or more visual markers do not appear in the display device.

3. The system of claim 2, wherein the model is fixed with respect to the manipulator such that the model moves when the manipulator moves.

4. The system of claim 3, wherein the processing unit is configured to determine the position of the manipulator and the orientation of the manipulator in real-time with respect to the sensor.

5. The system of claim 4, wherein the model appears to be contained within the manipulator rather than appearing on the outer surface of the manipulator.

6. The system of claim 4, wherein the manipulator comprises a cube with a plurality of rows and columns of the one or more visual markers on each side.

7. The system of claim 4, wherein the processing unit, the sensor, and the display device are a single apparatus that is designed to be mounted on a head of a user.

8. The system of claim 4, wherein the display device comprises glasses or goggles and is designed to be mounted on a head of a user.

9. The system of claim 8, wherein the display device is transparent.

10. A method for modelling a portion of a patient, comprising:
    receiving first patient data corresponding to a first patient from a medical imaging device;
    receiving second patient data corresponding to a second patient from the medical imaging device
    processing the first patient data to generate a first model of the first patient;
    processing the second patient data to generate a second model of the second patient;
    receiving manipulator data from a sensor;
    processing the manipulator data to determine a position of a manipulator, an orientation of the manipulator, or both;
    displaying the first model within the manipulator on a display device using the processed first patient data and the processed manipulator data; and
    subsequently displaying the second model within the same manipulator on the display device using the processed second patient data on the processed manipulator data.

11. The method of claim 10, further comprising moving the manipulator with respect to the sensor, wherein the model is fixed with respect to the manipulator such that the model moves when the manipulator moves.

12. The method of claim 11, wherein moving the manipulator comprises rotating the manipulator, causing the model to rotate together with the manipulator.

13. The method of claim 10, wherein moving the manipulator comprises varying a distance between the manipulator and the sensor, causing a size of the manipulator and the model to vary on the display device.

14. The method of claim 10, further comprising removing a first portion of the model on or in the manipulator when the manipulator is displayed on the display device.

15. The method of claim 14, wherein removing the first portion of the model comprises touching the first portion of the model on the manipulator.

16. The method of claim 14, wherein a second portion of the model increases in size after the first portion of the model is removed.

17. The method of claim 10, further comprising triggering an action by shaking the manipulator or touching a virtual button on the manipulator.

18. The method of claim 17, wherein the action is selected from the group consisting of saving a view of the manipulator and the model as a screenshot, saving the view of the manipulator and the model as a video, and requesting a remote consultation.

19. The method of claim 10, further comprising placing the display device on a user's head.

20. The method of claim 10, wherein the first patient data is captured by the medical imaging device before a surgery, and wherein the method further comprises:
   removing a portion from the first patient, or adding the portion to the first patient, during the surgery;
   receiving additional first patient data corresponding to the first patient from the medical imaging device during or after the surgery;
   processing the additional first patient data to generate an additional first model of the first patient with the portion removed or added; and
   displaying the additional first model within the manipulator on the display device using the processed additional first patient data and the processed manipulator data.

21. The method of claim 10, wherein the first patient data is captured by the medical imaging device during a surgery, and wherein the first model comprises a surgeon's hand, a surgical instrument, or both in real-time as the surgery is being performed.

22. The method of claim 10, further comprising:
   moving the manipulator closer to the sensor, which causes the first model to increase in size within the manipulator on the display device; and
   moving the manipulator farther from the sensor, which causes the first model to decrease in size within the manipulator on the display device.

* * * * *

UNITED STATES PATENT AND TRADEMARK OFFICE
CERTIFICATE OF CORRECTION

PATENT NO. : 11,369,440 B2
APPLICATION NO. : 16/605421
DATED : June 28, 2022
INVENTOR(S) : Bernhard Fuerst et al.

It is certified that error appears in the above-identified patent and that said Letters Patent is hereby corrected as shown below:

On the Title Page

Item (73) Under Assignee, "The John Hopkins" should be -- The Johns Hopkins --

Signed and Sealed this
Fourteenth Day of March, 2023

Katherine Kelly Vidal
*Director of the United States Patent and Trademark Office*